United States Patent [19]
Arav

[11] Patent Number: 5,873,254
[45] Date of Patent: Feb. 23, 1999

[54] DEVICE AND METHODS FOR MULTIGRADIENT DIRECTIONAL COOLING AND WARMING OF BIOLOGICAL SAMPLES

[75] Inventor: Amir Arav, Tel Aviv, Israel

[73] Assignee: Interface Multigrad Technology, Migdal Haemek, Israel

[21] Appl. No.: 709,350

[22] Filed: Sep. 6, 1996

[51] Int. Cl.$^6$ ........................................ F25D 13/06
[52] U.S. Cl. ................... 62/63; 62/64; 62/65; 62/374; 62/380
[58] Field of Search .................. 62/63, 64, 65, 62/78, 378, 81; 165/381

[56] References Cited

U.S. PATENT DOCUMENTS

| | | | |
|---|---|---|---|
| 4,972,681 | 11/1990 | Lofkvist | 62/374 |
| 5,630,321 | 5/1997 | Miller | 62/63 |

OTHER PUBLICATIONS

Arav, A., "Vitrification of Oocytes and Embryos", found in Embronic Development and Manipulation, Eds. Lauria & Gandalfi, Portland Press (1992), pp. 255–264.

Arav, A. et al, "Cyropreservation of Bovine Semen with Directional Solidification", *Cyrobiology*, Atlanta Meeting, (1993).

Rubinsky, B. et al, "Cyropreservation of Oocytes Using Directional Cooling and Antifreeze Glycoprotiens", *Cyro–Letters*, 12:93–106 (1991).

Rubinsky, B. et al, "A Cryomicroscope Using Directional Solidification for the Controlled Freezinf of Biological Material", *Cryobiology*, 22:55–68 (1985).

Brower, W.E. et al, "An Hypothesis for Survival of Spermatozoa Via Encapsulation During Plane Front Freezing", *Cryobiology*, 18: 277–291 (1981).

Beckmann J. et al., "Redefining Cooling Rate in Terms of Ice Front Velocity and Thermal Gradient: First Evidence of Relevance to Freezing Injury of Lymphocytes", *Cryobiology*, 27:279–287 (1990).

Hubel A. et al., "Survival of Directionally Solidified B–Lynphoblasts under Various Crystal Growth Conditions", *Cryobiology*, 29:183–198 (1992).

Arav A. et al., "The Role of Thermal Hysteresis Proteins During Cropreservation of Oocytes and Embryos", *Theriogenology*, 41:107–112 (1994).

Arav A et al., "Recent Developments in Cyropreservation of Stallion Semen with Special Emphasis on Thawing Procedure Using Thermal Hysteresis Proteins", *Zygote* 2(Nov. 1994) pp. 379–382.

Arav A. et al., "Arav A. et al., Crioconservazione Di Oociti Immaturi Di Maiale Mediante Vitrificzione", *Estratto Da Selezione Veterinaria*, 1991, vol. XXXII, n. 1 bis (Abs in English).

Arav A. et al., "Osmotic and Cytotoxic Study of Vitrification if Immature Bovine Oocytes", *J. Of Repro. and Fert.*, (1993) 99:353–358.

(List continued on next page.)

Primary Examiner—Henry Bennett
Assistant Examiner—Pamela A. Wilson
Attorney, Agent, or Firm—Mark M. Friedman

[57] ABSTRACT

A device for controlled freezing and warming of a biological sample, and freezing and thawing protocols for which the device is well suited. The device establishes a laterally varying thermal gradient and provides a mechanism for moving the sample along the thermal gradient at a controlled rate of speed. The sample is moved along the thermal gradient at a rate of speed that provides a variable cooling rate or a variable warming rate in accordance with the appropriate protocol. The device also allows continuous seeding of the sample through the freezing process at the exact freezing point of the solution. Real time monitoring and video imaging of the freezing process enable fine tuning of the thermodynamic parameters for improved control.

16 Claims, 4 Drawing Sheets

OTHER PUBLICATIONS

Koebe et al, "Temperature Gradients in Freezing Chambers of Rate–Controlled Cooling Machines" *Cryobiology*, 30, 349–352 (1993).

Fiser, P.S. et al., "The Effect of Induced Ice Nucleation (Seeding) on the Post–Thaw Motility and Arosomal Integrity of Boar Spermatozoa", *Animal Repro. Science*, 24:293–304 (1991).

Luyet, et al, "A Critical Temperature Range Apparently Characterized By Sensitivity of Bull Semen To High Freezing Velocity", *Biodynamica*, vol. 7, No. 152, pp. 281–292 (1955).

Weitze et al., "Fertility of Frozen Boar Semen: Influence of Packaging, Number of Inseminations, and Seminal Plasma", no publishing info given.

Shabana et al, "Fluorometric Analysis of Transient Solute Redistribution Fields During Freezing of Aqueous Solutions" Advances in Cryobiology and Cryomedicine (1995).

DEVICE AND METHODS FOR MULTIGRADIENT DIRECTIONAL COOLING AND WARMING OF BIOLOGICAL SAMPLES

FIELD AND BACKGROUND OF THE INVENTION

The present invention relates to the controlled freezing of biological samples consisting of cells and tissues, such as semen, oocytes, and embryos; and, more particularly, to a directional freezing device that sets up a laterally varying temperature gradient, and freezing and thawing protocols allowed by the device.

When a biological sample containing living cells in a freezing solution is frozen, the first portion of the sample to freeze is the intercellular fluid. The formation of ice in the intercellular fluid increases the salt concentration there. If the sample is frozen too slowly, the high concentration of salt in the intercellular fluid may kill the cells, by osmotic shock or by chemical toxicity. Conversely, freezing the sample too rapidly may lead to the formation of intracellular ice crystals, which also kill the cell, by internal mechanical damage. In addition, the rate of cooling affects the morphology of the intercellular ice crystals. Morphologies such as closely packed needles also kill cells, by external mechanical damage. Thus, maximizing the survival rate of cells subjected to freezing and thawing requires careful control of the freezing process.

An alternative method of freezing biological samples, which totally avoids the problems associated with ice crystal formation, is to cool them so fast that the intercellular and intracellular fluids vitrify instead of crystallizing as ice. This method has dangers of its own, however. In particular, the rate of cooling is so fast that, because of thermal shock, glass fractures may form within the sample at temperatures below its glass transition temperature. To prevent ice crystal formation upon thawing, vitrified samples must be warmed as fast as they were cooled, so thermal shock may cause fracture formation either during the cooling process or during the warming process.

The conventional method for freezing biological samples is to place them in a chamber and lower the temperature of the chamber in a controlled manner. Samples frozen in this manner freeze from the outside in. The thermal gradient within the sample is determined implicitly by the temperature of the chamber and the thermal conductivities of the materials within the sample, and is not explicitly controllable. This makes it difficult to achieve the optimal cooling rate, which minimizes both the toxicity associated with cooling too slowly and the mechanical damage associated with cooling too fast.

Rubinsky, in U.S. Pat. No. 4,531,373, introduced controlled directional freezing, in which a sample is placed on a microscope slide, and the microscope slide is moved longitudinally through a region of substantially constant temperature gradient $dT/dx$ (T denoting temperature and x denoting distance). If the microscope slide is moved through the temperature gradient at a constant speed $V=dx/dt$, where t denotes time, then each point in the sample cools at a rate of $dT/dt=V*(dT/dx)$. Using Rubinsky's method, the rate of cooling of each point in the sample is subject to explicit control. In addition, if the cooling is done on a microscope stage, the sample can be monitored in detail for undesired phenomena such as the formation of intracellular ice.

Rubinsky's method, having only one uniform thermal gradient, is inherently limited to cooling at a single rate. Thus, it is unsuitable for cooling protocols that require different rates in different temperature ranges. For example, Arav ("Vitrification of oocytes and embryos", in Embryonic Development and Manipulation (Lavria and Gandalfi, editors), Portland Press, 1992, pp. 255–264) recommends that vitrification be done with rapid cooling above the glass transition temperature and slower cooling below the glass transition temperature. In addition, Rubinsky's use of a microscope stage for monitoring makes his device unsuitable for commercial or industrial scale production, or for the use of commercial cell packaging ("straws").

There is thus a widely recognized need for, and it would be highly advantageous to have, a device for directional cooling of a biological sample by moving the sample through regions of laterally varying temperature gradient, and associated freezing and thawing protocols that exploit the ability to cool and thaw at different rates in different temperature ranges.

SUMMARY OF THE INVENTION

According to the present invention there is provided a device for freezing a biological sample, comprising: (a) a track; (b) refrigeration means for imposing a laterally variable temperature gradient along the track; and (c) a mechanism for moving the biological sample along the track.

According to the present invention there is provided a method for freezing a biological sample having a freezing temperature, comprising the steps of: (a) placing the biological sample inside a straw having a leading end; (b) moving the straw from a warm region having a first temperature higher than the freezing temperature to a cold region having a second temperature lower than the freezing temperature, the leading end of the straw entering the cold region before any other part of the straw; and (c) freezing the leading end of the straw before the leading end of the straw enters the cold region.

According to the present invention there is provided a method for freezing a semen sample having a lipid phase transition temperature, the sample being initially at a temperature above the lipid phase transition temperature, the method comprising the steps of: (a) cooling the sample to an intermediate temperature slightly below the lipid phase transition temperature at a rate sufficiently slow to prevent chilling injury; and (b) cooling the sample below the intermediate temperature at a rate of between about 30° C. per minute and about 1500° C. per minute.

According to the present invention there is provided a method for freezing a biological sample having a glass transition temperature, the sample being initially at a temperature above the glass transition temperature, the method comprising the steps of: (a) cooling the sample to about the glass transition temperature at a rate sufficiently fast to prevent ice formation; and (b) cooling the sample below about the glass transition temperature at a rate sufficiently slow to prevent glass fracturing.

According to the present invention there is provided a method of warming a biological sample having a glass transition temperature, the sample being initially at a temperature below the glass transition temperature, the method comprising the steps of: (a) warming the sample to about the glass transition temperature at a rate sufficiently slow to prevent glass fracturing; and (b) warming the sample above about the glass transition temperature at a rate sufficiently fast to prevent devitrification.

The preferred embodiment of the device of the present invention is a series of copper blocks arranged in a line, with a straight track running through the blocks. Each block is equipped with a refrigerator to cool the block, and optionally one or more heaters to warm the block. In the simplest configuration, the refrigerator is on one side of the block and one heater is on the other side of the block, thereby imposing a temperature gradient on the portion of the track contained in the block. In another configuration, the refrigerator cools the block as a whole, and two or more heaters impose a temperature gradient along the portion of the track contained in the block. The blocks are separated by gaps, and the temperature of the block on one side of the gap typically is different from the temperature on the other side of the gap, thereby imposing a temperature gradient across the gap. Biological samples to be frozen or thawed are placed inside straws, and the straws are moved along the track at speeds such that the samples are frozen or thawed at rates specified by protocols specific to the samples. Monitoring devices, such as CCD video cameras coupled to microscope objectives, and such as infrared thermographs, are deployed at the gaps to monitor the progress of the freezing or thawing.

In a variant of this preferred embodiment, the blocks are mounted in the neck of a dewar of liquid nitrogen, with the entrance (high temperature end) of the track at or above the top of the neck, and the exit (low temperature end) of the track within the neck or at the base of the neck. When the straws reach the exit, they fall into the liquid nitrogen for long term storage.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a cooling device which can be used for the controlled freezing and thawing of biological samples, and of protocols for its use with various kinds of samples. Specifically, the device of the present invention can be used to move biological samples through regions of laterally varying temperature gradients, thereby effecting cooling and thawing at controlled rates.

The principles and operation of a cooling device according to the present invention may be better understood with reference to the drawings and the accompanying description.

Figure 1A:
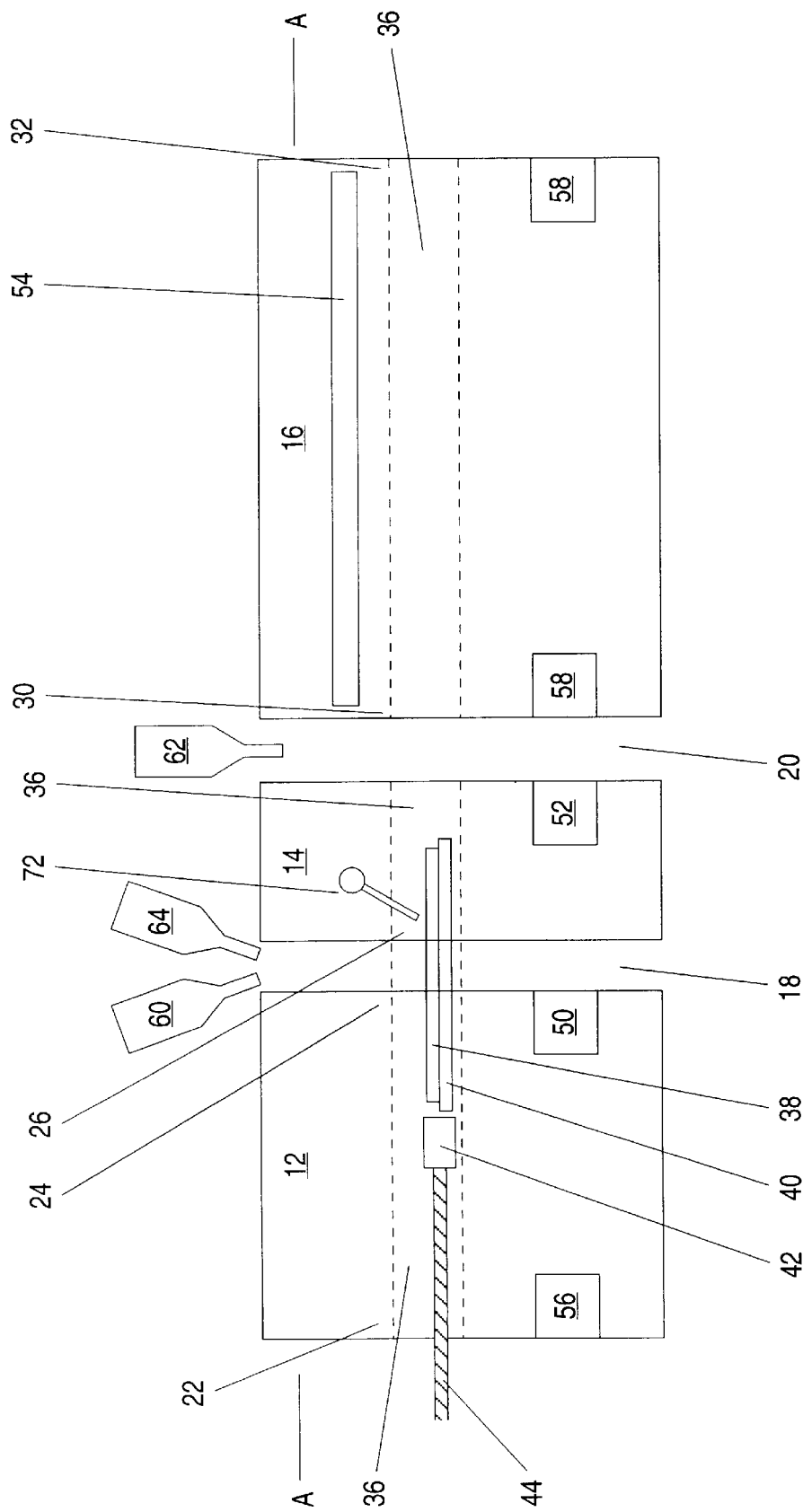
FIG. 1A is a schematic side view of a preferred embodiment of the device of the present invention, based on thermally conductive blocks.

Referring now to the drawings, FIG. 1A is a schematic side view of one preferred embodiment of the device of the present invention. Three blocks 12, 14, and 16, of a thermally conductive material, preferably copper, are arranged in a line. Block 12 is about 16 centimeters long. Block 14 is about 2.5 centimeters long. Block 16 is about 10 centimeters long. Blocks 12 and 14 are separated by a gap 18. Blocks 14 and 16 are separated by a gap 20. Gaps 18 and 20 may be between 0.01 centimeters and 1.5 centimeters wide. A tunnel 36, preferably of rectangular cross section, runs through blocks 12, 14, and 16. Tunnel 36 defines a track along which a sled 40 is moved. Sled 40 preferably is made of a thermally conductive material, preferably copper, and bears one or more straws 38 that contain biological samples to be frozen or thawed. Straws 38 typically are hollow tubes of circular or rectangular cross section, about 14 to 30 centimeters long. Sled 40 is moved through tunnel 36 by a piston 42 to which is attached a helically threaded rod 44. Rod 44 is moved to the right by a screw drive (not shown).

Blocks 12 and 14 include refrigerators 50 and 52. Blocks 12 and 16 include heaters 56, 57 and 58. Refrigerators 50 and 52 operate conventionally, by compressing and expanding cryogenic fluids. Heaters 56, 57 and 58 typically are electrical resistance heaters. Block 16 includes a channel 54 through which liquid nitrogen is circulated. Refrigerator 50 and heater 56 serve to impose a temperature gradient on the portion of tunnel 36 that runs from warm side 22 of block 12 to cold side 24 of block 12. Refrigerator 52 imposes a substantially constant temperature on block 14. The effect of the liquid nitrogen in channel 54 and heaters 57 and 58 is to impose a temperature gradient on the portion of tunnel 36 that runs from warm side 30 of block 16 to cold side 32 of block 16. The temperatures within blocks 12, 14, and 16 are monitored by thermocouples (not shown) and controlled by feedback loops (not shown) that include refrigerators 50 and 52 and heaters 56, 57 and 58.

In general, gaps between blocks of the present invention, such as gaps 18 and 20 separating blocks 12, 14, and 16, preferably are no wider than 1.5 centimeters. In that way, the tunnel, such as tunnel 36, through the blocks encloses substantially all of the track along which the biological samples move, isolating the samples from the outside environment and helping to impose the thermal gradients of the blocks on the biological samples.

At gap 18, a video camera 60 and an infrared thermograph 64 are deployed for monitoring the condition of the biological sample in straw 38 as straw 38 traverses gap 18. Suitable infrared thermographs 64 include those made by Elbit Ltd. of Haifa, Israel, and the Microscanner D501 made by Exergen Co. of Newton Mass. Similarly, another video camera 62 is deployed at gap 20 for monitoring the condition of the biological sample in straw 38 as straw 38 traverses gap 20. Video cameras 60 and 62, and infrared thermograph 64, transmit signals to a monitor (not shown), on which an operator can observe the visual appearance and the temperature contours of the contents of straw 38. In production mode, most straws 38 are opaque. For the purpose of visual monitoring for quality control, some of straws 38 are special transparent (typically glass) straws of rectangular cross section. Infrared thermograph 64 monitors the temperature profile of all straws 38.

Block 14 is provided with a channel 72 for applying liquid nitrogen to straw 38 to seed freezing, as described below.

Figure 1B:
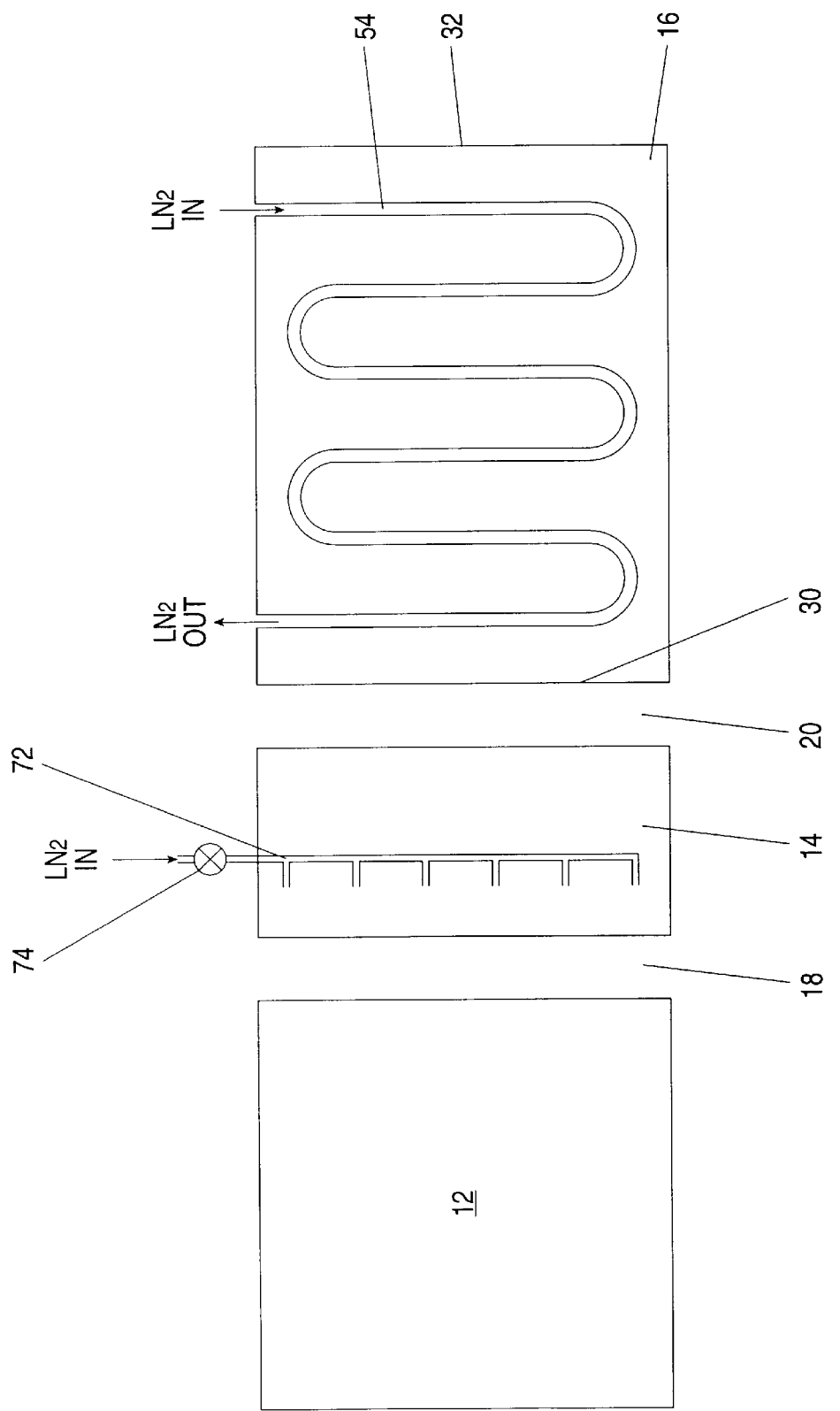
FIG. 1B is a schematic cross sectional view of the preferred embodiment of FIG. 1A.

FIG. 1B is a schematic cross sectional view of the preferred embodiment of FIG. 1A, taken along cut A—A. FIG. 1B shows that the geometry of channel 54 in block 16 is that of a coil open at both ends, with liquid nitrogen entering channel 54 at the end nearer to cold side 32 of block 16 and exiting channel 54 at the end nearer to warm side 30 of block 16. FIG. 1B also shows that channel 72 in block 14 is provided with an electrically activated valve 74 to admit liquid nitrogen. The variant of channel 72 shown in FIG. 1B is capable of seeding six straws 38 at once.

Figure 2:
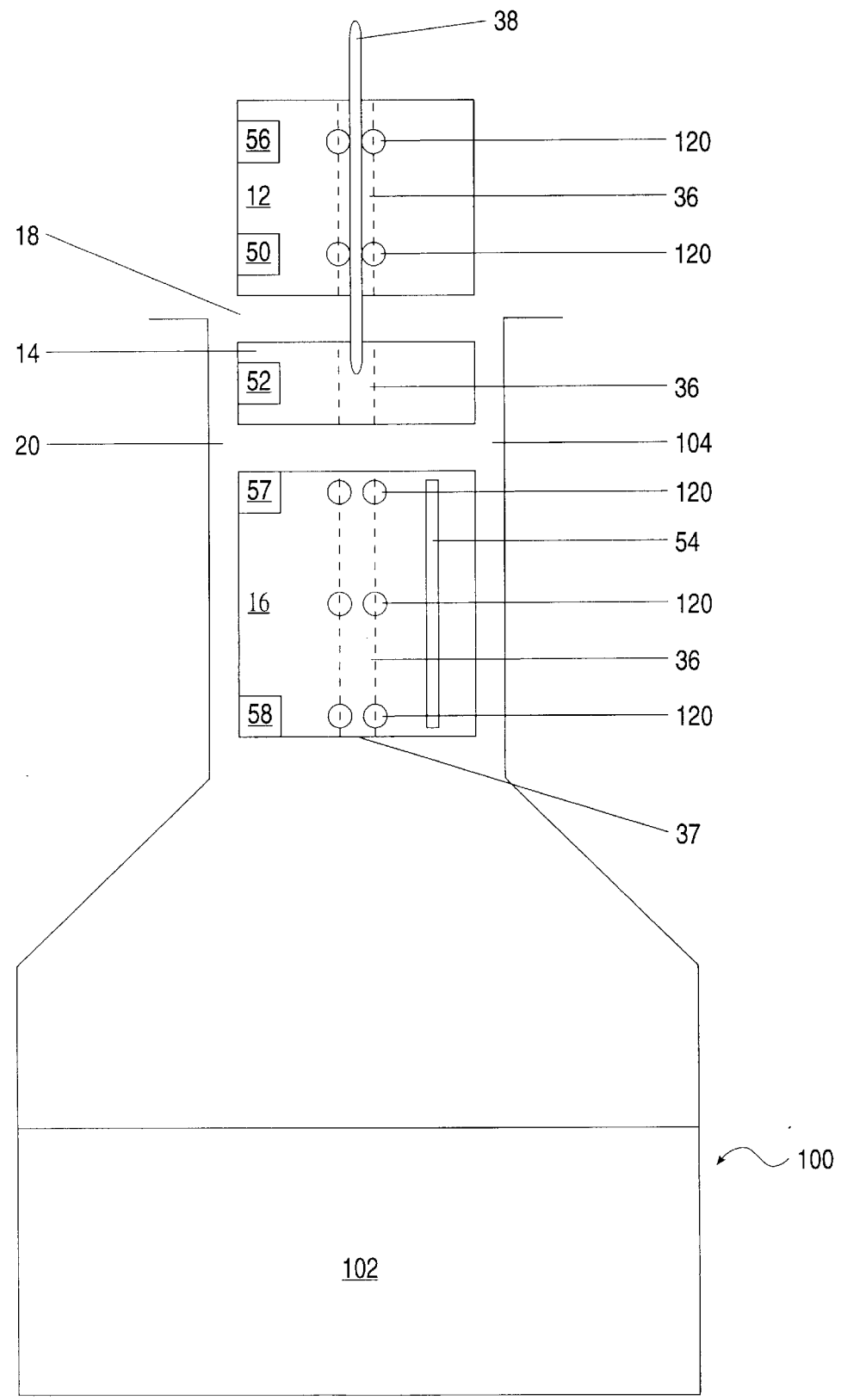
FIG. 2 is a schematic diagram of a variant of the device of FIG. 1A.

FIG. 2 is a schematic view of a variation of the device of FIGS. 1A and 1B. In this variation, blocks 12, 14, and 16 are mounted in a neck 104 of a dewar 100 of liquid nitrogen 102. Refrigerators 50 and 52, and heaters 56, 57 and 58 are thermoelectric devices, rather than conventional cryogenic refrigerators or resistance heaters. Tunnel 36 is circular in cross section; and, instead of providing sled 40 to move straw 38 laterally along the track defined by tunnel 36, as in FIG. 1A, pairs of rollers 120 are provided that grip straw 38 frictionally and move straw 38 downwards through tunnel 36. When straw 38 emerges from exit 37 of tunnel 36, straw 38 falls into liquid nitrogen 102 for preservation.

The device of the present invention enables the implementation of controlled seeding in the freezing of biological samples. When any liquid is cooled below its freezing point, it remains a liquid, in an unstable supercooled state, for at least a short time. Freezing starts at nucleation sites that are distributed substantially randomly throughout the volume of the liquid, and spreads through the rest of the liquid. In the conventional, equiaxial (nondirectional) method of freezing biological samples, ice grows with uncontrolled velocity and morphology, and may disrupt and kill the cells of the samples.

Directional freezing allows controlled nucleation, or seeding, of freezing, at least in principle. As a straw containing a biological sample is moved forward along a thermal gradient, from a temperature above the freezing point of the sample to a temperature below the freezing point of the sample, at some point in time, the leading edge of the straw reaches a point in space at which the temperature is below the freezing point of the sample. The leading end of the straw is now frozen, for example by touching it with a cold object such as a small amount of liquid nitrogen. Uncontrolled freezing proceeds backwards along the straw to the point in space at which the temperature is equal to the freezing point of the sample. As the straw continues to move forward, the frozen part of the sample nucleates freezing of the liquid part of the sample as the liquid part of the sample passes the point in space at which the temperature is equal to the freezing point of the sample. Thus, uncontrolled freezing, with consequent random destruction of cells, is confined to a small region at the leading end of the straw, and controlled freezing occurs at a freezing front that moves backwards along the straw but remains substantially stationary with respect to the thermal gradient, substantially at the point along the thermal gradient at which the temperature is equal to the freezing point of the sample.

Ideally, the velocity of the freezing front should be such that the ice morphology does not disrupt the cells of the biological sample. This is difficult to achieve using the directional freezing devices of the prior art, which have laterally constant gradients, because the rate of cooling consistent with favorable ice morphology may not be consistent with other desired cooling rates of a sample's freezing protocol. The laterally varying gradient of the device of the present invention allows cooling at different rates in different temperature regimes, thereby allowing fully controlled nucleation at the freezing front. For example, a short part of the thermal gradient, immediately to the cool side of the point at which the temperature is equal to the freezing point of the sample, can be set equal to zero, providing a short region of constant temperature slightly below the freezing point of the sample. If the sample is a suspension of separate cells, then this constant temperature is slightly below the freezing temperature of the freezing solution in which the cells are suspended. If the sample is a tissue sample, then this constant temperature is slightly below the freezing temperature of the tissue sample. Note that in the context of the present invention, "slightly below" means lower in temperature by between about 1° C. and about 10° C. This now will be illustrated in the context of the use of the device of FIG. 1 for freezing oocytes and embryos.

The prior art protocol for freezing oocytes and embryos is to cool from 0° C. to −7° C. at a rate of between about 0.5° C. per minute and about 10° C. per minute, but most preferably at a rate of about 1° C. per minute; and from −7° C. to −35° C. at a rate of between about 0.1° C. per minute and about 1.5° C. per minute, but most preferably at a rate of about 0.3° C. per minute. The present invention allows this protocol to be effected directionally. The present invention also allows this protocol to be applied to the directional freezing of ovarian cortical tissue. The ovarian cortical tissue is removed surgically from the patient (typically a woman about to undergo chemotherapy or radiation therapy) and sliced into slices having a dimension of about 1 cm×1 cm×0.5 mm. These slices are frozen inside specially dimensioned flat straws 38 having rectangular cross sections about 1 cm wide and about 2 mm high.

Figure 3:
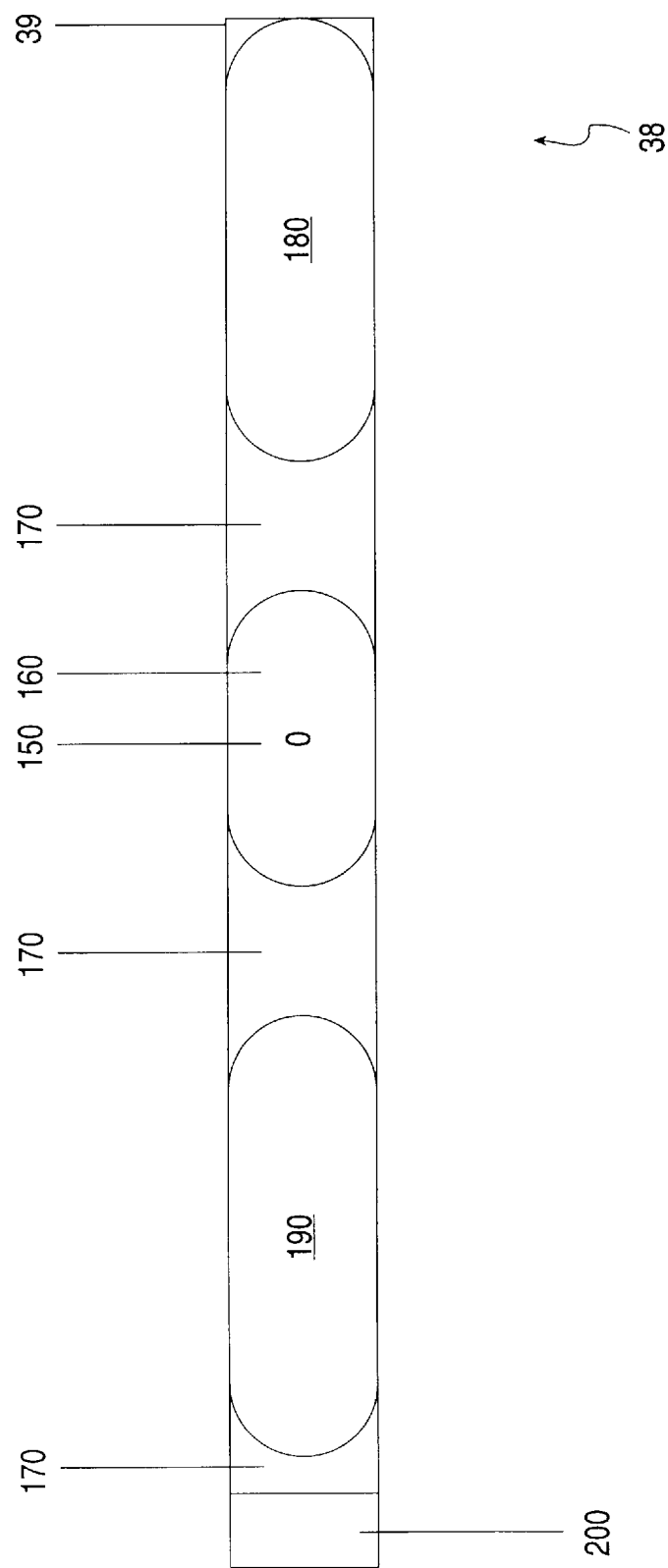
FIG. 3 shows the manner in which a sample of embryos or oocytes is loaded in a straw.

Straw 38 is loaded as shown in FIG. 3. A sample 150, containing one or more oocytes or embryos, is placed in the middle of straw 38, surrounded by about 10 to 100 microliters 160 of freezing solution. One end 39 of straw 38, which is the leading end as straw 38 travels through tunnel 36, is plugged with a cotton plug 180 saturated with freezing solution. The other end of straw 38 is filled with sucrose solution 190 and sealed with seal 200. Plug 180, sample-bearing freezing solution 160, sucrose solution 190, and seal 200 are separated by air bubbles 170 as shown.

Refrigerator 50 and heater 56 are set to give block 12 a temperature of 22° C. at warm side 22 and a temperature of 0° C. at cold side 24. Refrigerator 52 is set to give block 14 a uniform temperature of −7° C. Heaters 57 and 58 are set to give warm side 30 of block 16 a temperature of −10° C. and cold side 32 of block 16 a temperature of −35° C. For this protocol, the width of gap 18 is set to 0.84 centimeters, and the width of gap 20 is set to 1.2 centimeters.

Straw 38 is placed on sled 40, the side of sled 40 bearing leading end 39 of straw 38 is placed inside tunnel 36 at warm end 22 of block 12, and sled 40 is moved through tunnel 36, using piston 42 and rod 44, at a speed of 20 microns per second. When leading end 39 of straw 38 enters end 26 of block 14, valve 74 is opened for between about 5 seconds and about 10 seconds, allowing a small amount of liquid nitrogen to touch leading end 39 of straw 38, thereby seeding the freezing of the contents of straw 38. Because blocks 12 and 14 and sled 40 are made of a thermally conductive material such as copper, the imposition of a temperature of 0° C. at cold end 24 of block 12 and of −7° C. throughout block 14 sets up a substantially linear temperature gradient, of −8.3° C. per centimeter, in the portions of sled 40 and straw 38 that occupy gap 18. As straw 38 moves across gap 18, freezing proceeds in the opposite direction within straw 38, with a freezing front established at the point in gap 18 where the temperature is the freezing point of the solutions contained in straw 38, about −3° C. (In air bubbles 170, the freezing front propagates via fluid that wets the inner wall of straw 38.) As sample 150 crosses gap 18, it is cooled from 0° C. to −7° C. at the desired rate of 1° C. per minute. Video camera 60 and infrared thermograph 64 are used to monitor the morphology and location of the freezing front in gap 18, so that the speed at which straw 38 is moved across gap 18 can be fine-tuned. The temperature of sample 150 stays constant at −7° C. as sample 150 moves through block 14. As sample 150 enters block 14, the speed of sled 40 is increased to about 40 microns per second, so that sample 150 spends about 10 minutes inside block 14 at a constant temperature of −7° C. When sample 150 emerges from block 14, it is in a region, including both gap 20 and block 16, in which the temperature gradient is about −2.5°

C. per centimeter. At this point the speed of sled 40 is reduced to the original 20 microns per second, so that sample 150 reaches cold end 32 of block 16, at which the temperature is −35° C., in about 93 minutes, i.e., at the desired rate of 0.3° C. per minute. Video camera 62 monitors the morphology of the contents of straw 38 as straw 38 emerges from block 14 into gap 20, to make sure that the contents of straw 38 are entirely frozen and that sample 150 has not been damaged mechanically by the freezing process.

In the case of other kinds of biological samples, such as bull semen, straw 38 is substantially entirely filled with the sample to be frozen. In that case, seeding by quickly freezing one end of straw 38 inevitably kills the part of the sample being frozen in the seeding process. Nevertheless, the rest of the sample may be frozen in a controlled manner, and significantly more of the sample survives freezing and thawing than in the conventional, nondirectional freezing method.

The above protocol is conventional; the advantage of implementing it using the device of the present invention is that it can be implemented directionally. The present invention also includes other freezing and thawing protocols that can be effected only through the use of the device of the present invention. These include:

Semen (including bull, ram, goat, stallion, and human semen): Cool from 30° C. to an intermediate temperature slightly below the lipid phase transition temperature of the semen at a rate slow enough to prevent chilling injury, preferably about 1° C. per minute. Cool from the intermediate temperature to −50° C. at a rate of between about 30° C. per minute and about 1500° C. per minute. In the case of bull semen, the preferred intermediate temperature is about 5° C. This is faster than the conventional protocol for bull semen, which prescribes a cooling rate of only 30° C. per minute between 0° C. and −50° C. The preferred range of velocities for directional cooling under this protocol is between about 50 microns per second and about 3000 microns per second.

Vitrification: Cool from 30° C. to slightly below the glass transition temperature (typically about −110° C.) at a rate fast enough to prevent ice formation, at least about 100° C. per minute, but preferably at a rate of about 8400° C. per minute. Cool from slightly below the glass transition temperature to the temperature of liquid nitrogen at a rate of at most about 10° C. per minute, to avoid fracturing the sample by thermal shock.

Warming a vitrified sample stored in liquid nitrogen: Warm from the temperature of liquid nitrogen to slightly below the glass transition temperature at a rate of at most about 10° C. per minute, to avoid fracturing the sample by thermal shock. Warm from slightly below the glass transition temperature to 30° C. at a rate fast enough to prevent devitrification, at least about 100° C. per minute, but preferably at a rate of about 8400° C. per minute. This is safer than the conventional method of heating the sample in a water bath at a temperature between 55° C. and 75° C., because the danger of overheating inherent in the conventional method is avoided.

While the invention has been described with respect to a limited number of embodiments, it will be appreciated that many variations, modifications and other applications of the invention may be made.

What is claimed is:

1. A device for freezing a biological sample, comprising:
   (a) a track;
   (b) refrigeration means for imposing a laterally variable temperature gradient along said track, said refrigeration means including a plurality of thermally conductive blocks substantially enclosing said track; and
   (c) a mechanism for moving the biological sample along said track.

2. The device of claim 1, wherein said blocks are arranged linearly.

3. The device of claim 2, wherein said blocks are separated by gaps.

4. The device of claim 3, further comprising monitoring means deployed at said gaps.

5. The device of claim 4, wherein said monitoring means includes at least one video camera.

6. The device of claim 4, wherein said monitoring means includes at least one infrared thermograph.

7. The device of claim 1, wherein said refrigeration means includes at least one cryogenic fluid.

8. The device of claim 1, wherein said refrigeration means includes at least one thermoelectric device.

9. The device of claim 1, wherein said refrigeration means includes at least one electrical resistance heater.

10. The device of claim 1, wherein said mechanism for moving the biological sample includes a plurality of rollers.

11. The device of claim 1, wherein said mechanism for moving the biological sample includes at least one piston.

12. The device of claim 1, wherein said track has an exit, the device further comprising a container of liquid nitrogen, positioned to receive the sample as the sample emerges from said exit.

13. The device of claim 1, further comprising a seeding mechanism.

14. The device of claim 13, wherein said seeding mechanism includes at least one cryogenic fluid.

15. A device for freezing a biological sample, comprising:
   (a) a track having an exit;
   (b) refrigeration means for imposing a laterally variable temperature gradient along said track;
   (c) a mechanism for moving the biological sample along said track; and
   (d) a container of a cryogenic fluid, positioned to receive the sample as the sample emerges from said exit.

16. The device of claim 15, wherein said cryogenic fluid includes liquid nitrogen.

* * * * *